United States Patent [19]
Frantz et al.

[11] Patent Number: 6,109,265
[45] Date of Patent: Aug. 29, 2000

[54] ELASTIC MANDIBULAR ADVANCEMENT APPLIANCE

[76] Inventors: Don E. Frantz, 1004 4th St., League City, Tex. 77573; Michael D. Frantz, 1019 E. Foster Ave., Couer d'Alene, Id. 83814

[21] Appl. No.: 08/958,550

[22] Filed: Oct. 29, 1997

Related U.S. Application Data

[63] Continuation-in-part of application No. 08/493,926, Jun. 23, 1995, abandoned.

[51] Int. Cl.$^7$ ......................................................... A61F 5/56
[52] U.S. Cl. .......................... 128/848; 128/859; 128/862; 602/902
[58] Field of Search ..................................... 128/848, 846, 128/859–862; 602/902

[56] References Cited

U.S. PATENT DOCUMENTS

| | | | |
|---|---|---|---|
| 3,224,442 | 12/1965 | Stubbs | 128/859 |
| 3,536,069 | 10/1970 | Gores | 128/861 |
| 4,305,709 | 12/1981 | Bruhn | 128/861 |
| 4,413,978 | 11/1983 | Kurz | 433/6 |
| 4,505,672 | 3/1985 | Kurz . | |
| 5,082,007 | 1/1992 | Adell | 128/861 |
| 5,313,960 | 5/1994 | Tomasi | 128/848 |
| 5,365,945 | 11/1994 | Halstrom | 128/848 |
| 5,409,017 | 4/1995 | Lowe | 128/848 |
| 5,499,633 | 3/1996 | Fenton | 128/848 |
| 5,562,106 | 10/1996 | Hecke et al. | 128/848 |
| 5,570,704 | 11/1996 | Buzzard et al. | 128/848 |

FOREIGN PATENT DOCUMENTS

| | | | |
|---|---|---|---|
| 9428832 | 12/1994 | WIPO | 5/56 |

*Primary Examiner*—Michael A. Brown
*Assistant Examiner*—K Garnet
*Attorney, Agent, or Firm*—Browning Bushman

[57] ABSTRACT

There are disclosed two embodiments of a mandibular advancement or positioning device which uses elastic bands to pull the jaw forward. The appliance has an upper plastic tray conforming to the patient's upper teeth including maxillary dentition soft tissue and palate, and including a set of plastic retention hooks, one on the right and one on the left anterior buccal portion of the upper plastic base, with each extending outwardly from the tray. The appliance also has a lower plastic tray conforming to the patient's lower teeth including mandibular dentition and soft tissues, and including having a bite plane which opens the bite vertically. The lower tray also has a set of plastic retention hooks extending outwardly from the teeth, one on the right and one on the left of the posterior buccal portion of the lower plastic base. Specially formed elastic bands, are releasably attached to both the top and bottom retention hooks on both sides of the trays to pull the mandible forward for treatment of snoring and sleep apnea.

39 Claims, 6 Drawing Sheets

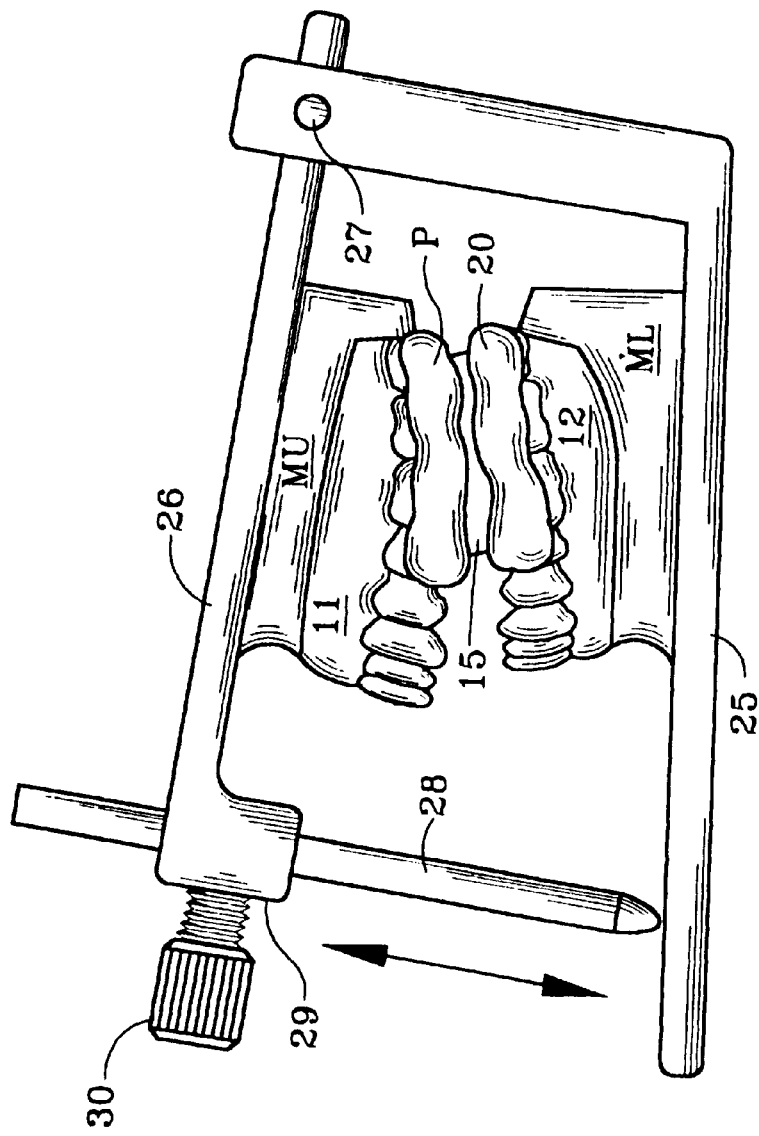
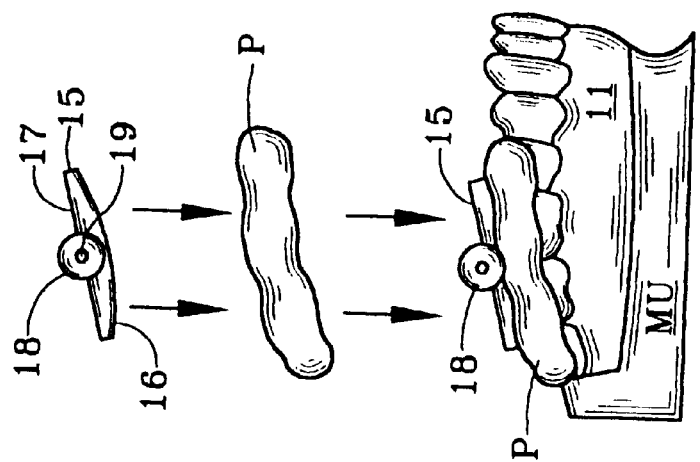
FIG. 9
FIG. 8

ELASTIC MANDIBULAR ADVANCEMENT APPLIANCE

This application is a continuation in part of our U.S. patent application Ser. No. 08/493,926, filed Jun. 23, 1995 now abandoned, and entitled "Elastic Mandibular Advancement Appliance.

BACKGROUND

1. Field

This invention related generally to oral appliances for preventing or at least alleviating snoring and sleep apnea. More specifically, this invention relates to a removable mandibular advancement appliance which uses elastic bands to pull the jaw forward and bite planes to open the bite vertically.

2. Related Art

It is well documented in the literature that an oral appliance that opens the bite and moves the mandible forward will greatly reduce sleep apnea and snoring. It is also documented that these appliances are capable of producing considerable discomfort to patients, unwanted movement of their teeth, and/or temporomandibular joint pain as well as other problems.

A variety of oral appliances are available for preventing snoring and sleep apnea. Of these, all are removable, and most advance the mandible, but, to our knowledge, none use elastic bands to move the mandible forward.

Also, several removable, oral snoring/apnea appliances are adjustable, pulling the jaw forward in different, set percentages of their maximum movement. However, no existing appliance known to us is totally adjustable, both in amount of forward movement and vertical opening. Instead, temporary or permanent adjustments to appliances are made by either soldering on spacers, or by grinding away plastic or other material. Once modifications are made, however, they are permanent until further modified by the doctor. In summary, appliances exist in which the amount of advancement may be changed, but the changes result in a modified appliance which advances the mandible to a new fixed position.

What is needed is totally adjustable, oral snoring/sleep apnea appliance which is effective, which has high patient acceptance, and which will not cause temporomandibular joint problems, unwanted tooth movement or soreness. This need is satisfied by the present invention.

The objective of the appliance of the present invention is to greatly reduce, or eliminate, sleep apnea and snoring, while alleviating temporomandibular joint problems, unwanted tooth movement and soreness, with complete adjustability of the appliance both in the amount of forward movement of the lower jaw, and in the amount of vertical bite opening. Another object is a mandibular advancement appliance with high patient acceptance, comfort, and treatment success.

SUMMARY OF THE INVENTION

The present invention is a totally adjustable, oral snoring/sleep apnea appliance. It is a mandibular advancement, or positioning, device which uses elastic bands to pull the jaw forward. It has a top section which is an upper plastic base or tray conforming to the patient's maxillary dentition, soft tissues and hard palate, the upper plastic or tray having a set of plastic retention hooks, one on the right side and one on the left side of the anterior buccal portion. Each retention hook extends outwardly from the teeth.

Also, the appliance of the present invention has a lower section which is a lower plastic base tray conforming to the patient's mandibular dentition, and soft tissues, the lower plastic tray having a set of posterior occlusal bite planes, one on each side. The lower plastic base or tray also has a retention hook extending outward from the teeth, one on the right and one on the left side of the posterior buccal portion. For reasons which will be understood from the description to follow, the hooks on the upper tray are forward of those on the lower tray.

Specially-formed elastic urethane bands, or standard orthodontic elastics are releasably attached to both the upper and lower retention hooks and of such length and/or elasticity that, when so attached, they will pull the mandible forward. Each set of urethane bands may have a slightly different length and different modulus of elasticity, for providing different advancement amounts.

The elastic mandibular advancement appliances of the present invention are removable oral devices and fit independently over the maxillary and mandibular dental arches, providing adjustable vertical mouth opening and variable anterior positioning of the mandible, which is incrementally adjustable via interchangeable urethane elastic bands, or standard orthodontic elastics, both of varying lengths and/or elasticity. This system allows for matching elastic pull to the opposing muscular forces. The elastic force may be increased, or decreased, in response to neuromuscular conditioning, or other factors. The appliances of the present invention provides medical and dental professionals with a non-surgical, non-invasive means of manipulating vertical and anterior positioning of the mandible as may be indicated in the treatment of Obstructive Sleep Apnea (OSA) and snoring. The adjustability of the elastic forces, and the freedom of lateral movement of the mandible, enables the appliance to give the patient comfort for the musculature and the temporomandibular joint heretofore unrealized.

The appliance of the present invention is fabricated using maxillary and mandibular thermal pressure formed plastic bases or trays, to which four (4) injection molded plastic retention hooks are bonded with orthodontic acrylic and two (2) bite planes. In a first embodiment of the invention, the bite planes are removable from the trays to permit them to be replaced with bite planes providing different vertical openings. In a second embodiment, in which the bite planes are fixed to the trays, the vertical opening is adjusted by grinding off their bite surfaces.

BRIEF DESCRIPTION OF THE DRAWINGS

FIG. 8 is a side view of the upper model and tray showing a removably bite plane made in accordance with the first embodiment of the invention being temporarily attached to the occlusal surface of the tray;

FIG. 9 is a side view of the upper and lower models removably mounted on a fixture in its closed and predetermined position to arrange the upper tray above the lower tray and with a body of acrylic disposed between the bottom side of the bite plane and occlusal surfaces of the lower tray;

DESCRIPTION OF THE PREFERRED EMBODIMENTS

Figure 1:
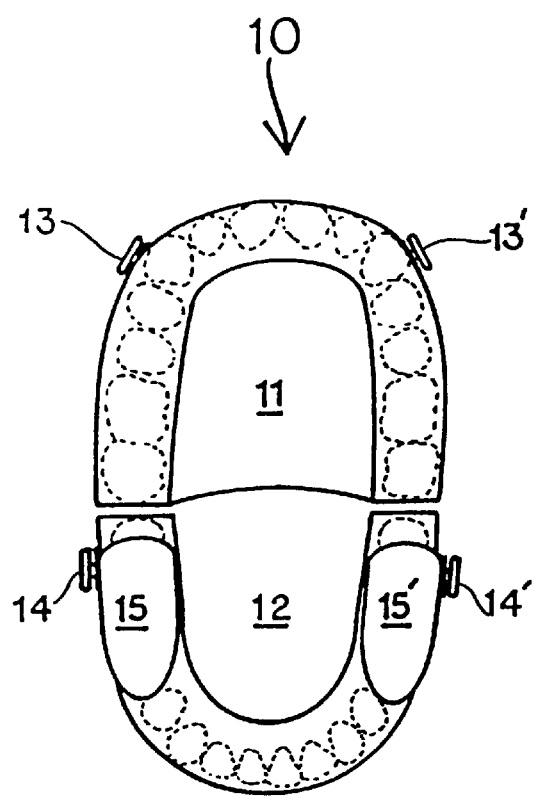
FIG. 1 is a schematic inside view of the upper and lower occlusal surfaces of the trays arranged end to end and made in accordance with a first embodiment of the appliance wherein the bite planes are removable, but with the hooks not being connected with elastic urethane bands.

Referring to the Figures, there is depicted in FIG. 1 the upper section or upper base or tray 11, and lower section or lower base or tray 12, of the first embodiment of the appliance 10, prior to connection of the upper and lower trays with elastic bands. On the outer sides of upper tray 11 are maxillary retention hooks 13 and 13', one located on each anterior buccal portion of upper tray 11, near the upper cuspid teeth. On the sides of lower tray 12 are mandibular retention hooks 14 and 14', one located on each posterior buccal portion of lower tray 12, near the lower molar teeth. Thus, as shown in FIGS. 1 and 2, the hooks 13 and 13' are generally aligned with one another, but are forward of the generally aligned hooks 14 and 14'.

On the posterior occlusal right and left surfaces of lower tray 12 are removable, interchangeable bite planes 15 and 15', each having a top side 16 providing a smooth surface engageable with the occlusal surface of the upper tray to space the occlusal surfaces from one another while permitting sliding movement of these surfaces laterally as well as longitudinally relative to one another. As will be described to follow, the bottom side 17 of each bite plane is formed for releasable attachment to a side of the lower tray.

Figure 2:
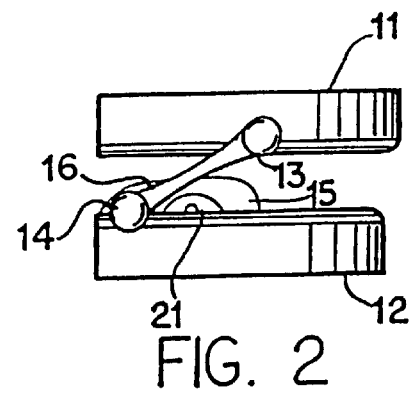
FIG. 2 is a schematic right side view of the upper and lower trays of the appliance of FIG. 1, arranged one above the other, and on the right side thereof with the hooks being connected together by an elastic urethane band.

There is depicted in FIG. 2 a right side view of upper tray 11, lower tray 12, maxillary retention hook 13, mandibular retention hook 14 and bite plane 15. In addition, maxillary retention hook 13 and mandibular retention hook 14 are interconnected by elastic band B, in a manner to be described to follow.

Figure 3A:
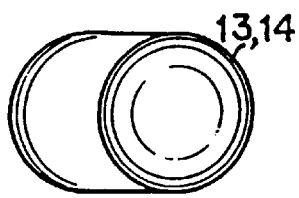
FIGS. 3A–C are top, bottom, and side views of the retention hook; component of the present invention.
Figure 3B:
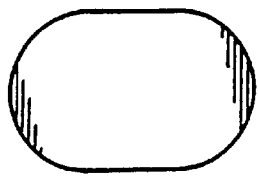
Figure 3C:
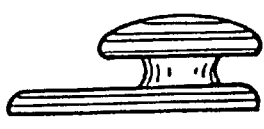

In FIGS. 3A–C are depicted different detail views of one of the retention hooks 13, 13', 14 and 14' used in the present invention. The retention hooks are bonded to the outer sides of the upper and lower trays 11 and 12, respectively, with orthodontic acrylic. The retention hooks are for the retention of elastic urethane bands or standard orthodontic elastics. The retention hooks are placed as follows: one (1) on the right and one (1) on the left of the anterior buccal (check) portion of the maxillary or upper tray; one (1) on the right and one (1) on the left of the posterior buccal (cheek) portion of the mandibular or lower tray. From the perspective of FIG. 2, FIG. 3A is an outside side view, FIG. 3B is an inside side view of the portion of the retention hook that is bonded to the base, and FIG. 3C is a top or bottom view of the retention hook. Each hook includes a base having an enlarged button on the outer thereof.

Figure 4:
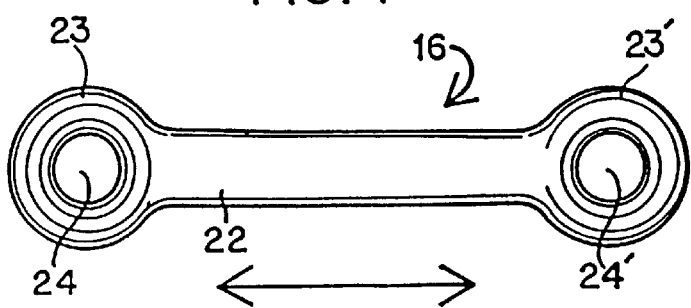
FIG. 4 is a detail view of an elastic urethane band.
Figure 5A:
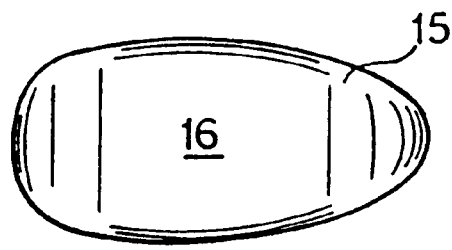
FIGS. 5A–D are top, bottom, end, and side detail views, respectively, of the illustrated bite plane of the present invention.
Figure 5C:
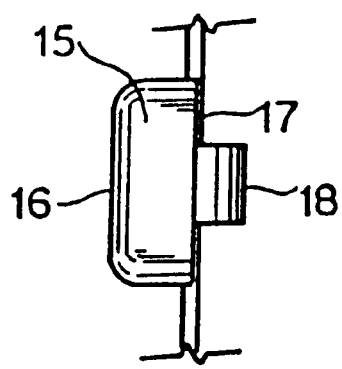
Figure 5B:
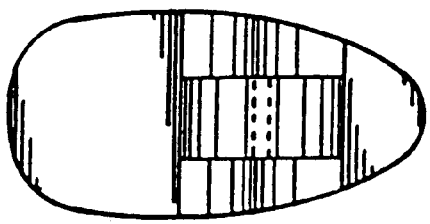
Figure 5D:
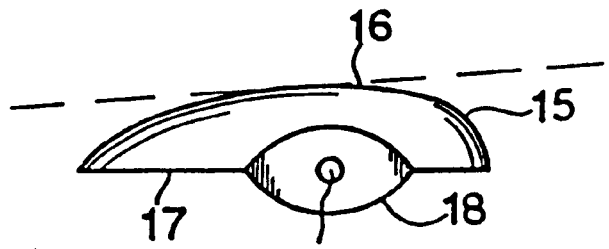

There is depicted in FIG. 4 a detail view of an elastic band B of the present invention. Band B has a central shaft portion 22 and two end portions 23 and 23', which are generally symmetric about the horizontal and vertical axes of band B. Both ends 23 and 23' have openings or holes 24 and 24' for closely receiving the buttons of the retention hooks 13, 13', 14 and 14'. Preferably, the length of band is about 15–30 mm from center to center of openings 24 and 24', the length and/or elasticity of the band being such that, when attached to the hooks, they are placed in tension or stretched as the appliance is installed in a patient's mouth so as to urge the lower jaw forwardly. Preferably, shaft portion 22 is about 2–4 mm thick, and ends 23 and 23' are about 3–6 mm thick. Preferably, ends 23 and 23' are thicker than the shaft portion 22, for a given band. In this way, the end portions may best resist the additional stresses caused by interconnecting the retention hooks in openings 24 and 24'.

Elastic band a is preferably made of injection molded urethane plastic, and different bands of different lengths and thicknesses and/or different elasticities may be provided to satisfy the patient's needs. Preferably, the specially-formed urethane bands have durometer hardness of about 55–85A. This way, the band has a firmer, more authoritative bias than is currently available from standard orthodontic elastics. Patient response has been very positive to embodiments of the subject invention with firm bands with durometer hardness within this 55–85A range. We think this is because the firmer bias of these elastic bands encourages the patient's musculature to relax, and not to fight or resist the bias.

In FIGS. 5A–5D are depicted detail views of an embodiment of a bite plane of the first embodiment of the present invention, namely one which has the surface of its top sides 16 at an elevation above the occlusal surface of one side of the tray to provide a vertical opening of 8 mm. As shown in FIG. 1, there are identical bite planes 15 and 15' on the opposite sides of the tray, although only one bite plane 15 will be described in detail.

Bite plane 15 may be made of injection molded plastic and has a generally smoothly curved, convex top contact surface 16, a generally flat bottom surface 17 and a tab 18 which depends from bottom surface 17 intermediate cut-out portions on both sides. Tab 18 is perforated with retention hole 19 for receiving a short strand of stainless steel wire 20. When the bite plane 15 is placed on the lower tray 12 of the appliance, tab 18 fits into a cooperating recess formed between arches on both sides of the occlusal surface of lower tray 12, as shown in FIG. 2. In each side of the arch of the lower tray 12 is a generally horizontal hole 21 (FIGS. 2 and 7), for receiving steel wire 20 which acts as an anchor to removably attach the bite plane 15 in place on tray 12.

The bite planes 15 and 15' are removably attached to the posterior occlusal right and left surfaces of the mandibular or lower tray. When it is desired to remove and replace the bite plane with a thicker or thinner bite plane, one simply inserts another wire or rod into horizontal hole 21, aligned with steel wire 20. Then, one pushes the steel wire 20 thought hole 21 and out the other side of the base with the other wire or rod, and withdraws the steel wire 20. This way, the steel wire 20 which anchors the bite plane 15 is removed, and horizontal hole 21 in the side of the lower base 12 is opened for accepting a replacement wire 20. This step is performed on both the right and left sides of the lower base 12.

Then, each of the replacement bite planes is placed on top of the lower base 12, with the bite plane's perforated tab 18 setting down in the cooperating recess in lower base 12, and the cut-outs resting on the arches to line up retention hole 19 with the horizontal holes 21 in lower base 12. Then, a steel wire 20 may be inserted in the horizontal hole 21, through retention hole 19, to provide an anchor for the replacement bite plane. After the steel wire 20 is inserted in the horizontal hole 21 in order to anchor the bite plane to the lower base 12, a rubber-based cement, like Silene™, for example, is preferably packed in the hole 21 between the wire 20 and the outside surface of base 12 to make a seal for sanitation and safety purposes.

Figure 6A:
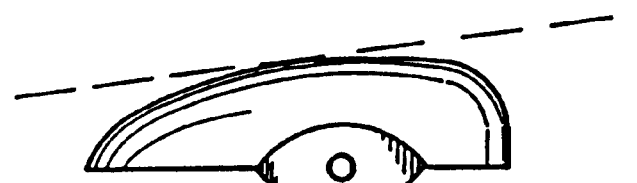
FIGS. 6A–C are side views of different sizes of bite planes of the present invention.
Figure 6B:
Figure 6C:

There are depicted in FIGS. 6A–C side views of different bite planes of the present invention, namely ones for vertical openings of 10, 12 and 14 mm, respectively. The bite planes are removable by removing the stainless steel wire holding them in place. Then, a different bite plane, one that is thicker or thinner for example, may be substituted in place of the original bite plane, and held in place by steel wire 20. The recommended bite plane will be the thinnest one that will relieve the sleep apnea and/or snoring and still provide for maximum patient comfort.

The above described appliance of the present invention is fabricated on a custom, per patient basis. In accordance with preferred procedures, the components necessary are: (1) two 0.060 (about 1.5 mm) or 0.080 inch (about 2 mm) thick sheets of clear PETG (FDA & USP Class 6 approved) plastic cut to fit the various vacuum/pressure forming machines (typically 125 mm squares or circles). (Although PETG is the currently preferred plastic, many different types of plastic are available, and certainly other types could work as well or better, or perhaps will become available in the future); (2) two posterior occlusal bite planes made of injection molded plastic, which are removably placed on the occlusal portion of the lower or mandibular tray, (4) four elastic retention hooks made of injection molded plastic, (2) two placed on the anterior of the maxillary tray, (2) two placed on the posterior of the hooks on the mandibular tray, beside the bite planes, bonded with orthodontic cold-cure acrylic (standard for fabricating retainers and ADA certified); and a variety of sizes and elasticity urethane bands or standard orthodontic elastics. These components will be offered in "kit" form for fabrication of the appliances in local labs and offices.

Initial Office Visit

Obtain an upper (maxillary) and lower (mandibular) impression of the teeth and supporting soft tissue including the upper hard palate. This impression must be extremely accurate to avoid tooth soreness, and/or movement when the appliance is placed in the patient's mouth. The impression is taken by: (1) having the patient rinse with a pre-impression mouth wash, like Muco Sole for example, to eliminate any saliva distortion; (2) taking impressions that extend beyond the most posterior molar teeth; (3) pouring the impressions immediately to avoid distortion using hard lab stone (Do not trim the models); (4) taking a was bite with the patient biting in a true centric occlusion. The professional then send the patient's models made from the impressions and wax bite to the lab.

Lab Procedure (1) The models are trimmed and mounted on a fixture, commonly known as a fixator, of such construction that the models may be removably mounted thereon from and returned to the fixator or other fixture with precision, while precisely maintaining a pre-set vertical opening and wax bite relation of the upper and lower models MU and ML. A typical fixator is shown in FIG. 9 as comprising a lower "L" shaped base 25 adapted to be supported in a generally horizontal position, and an arm 26 pivotally connected at 27 to the upper end of the upright of the base. The opposite free end of the arm carries a rod 28 with its end engaging the base when the fixture is closed, as in FIG. 9. The rod is slidable in a hole in a boss 29 at the end of the arm, and a set screw 30 is carried by the boss to permit the arm 26 to move to selected positions above the base, and thus to control the vertical spacing between the arm and horizontal portion of the base. Each of the models may be removably mounted on its respective arm or base in a desired position, vertically as well as longitudinally (right and left) with respect to the other model.

(2) The lab technician "waxes out" the undercuts on the trays so that the appliance will have the correct retention when inserted by the patient on the teeth.

(3) A clear sheet of 0.060 inch or 0.080 inch PETG plastic is placed in a thermo-pressure forming dental machine. The upper and then the lower models MU and ML are removed from the fixator and placed on this machine, and the plastic is pressure formed over the teeth and supporting soft tissues and palate of each model after the proper heat is applied to the plastic to form upper and lower trays 11 and 12.

(4) The models with their newly formed plastic trays are trimmed. On the maxillary or upper model, the plastic is trimmed 2–5 mm above the teeth on the labial and buccal surfaces and extends transpalatal distal to the first or second molars leaving the upper palate completely covered with the plastic sheet. On the mandibular or lower model, the plastic is trimmed 2–5 mm below the teeth on the labial, buccal, and lingual surfaces.

(5) The models, with their newly formed and trimmed plastic bases or trays are then returned and removably mounted on the fixator, as described in (1).

(6) The arm of the fixture is adjusted to open the bite 10 mm. As diagrammatically shown in FIG. 8, each bite plane is positioned and temporarily mounted (via sticky wax or putty P) to the posterior occlusal surfaces of the maxillary (upper) plastic base or tray. For reasons which will be apparent to follow, in the first embodiment of the invention, the bite planes 15 are molded of a material to which acrylic does not bond.

Figure 7:
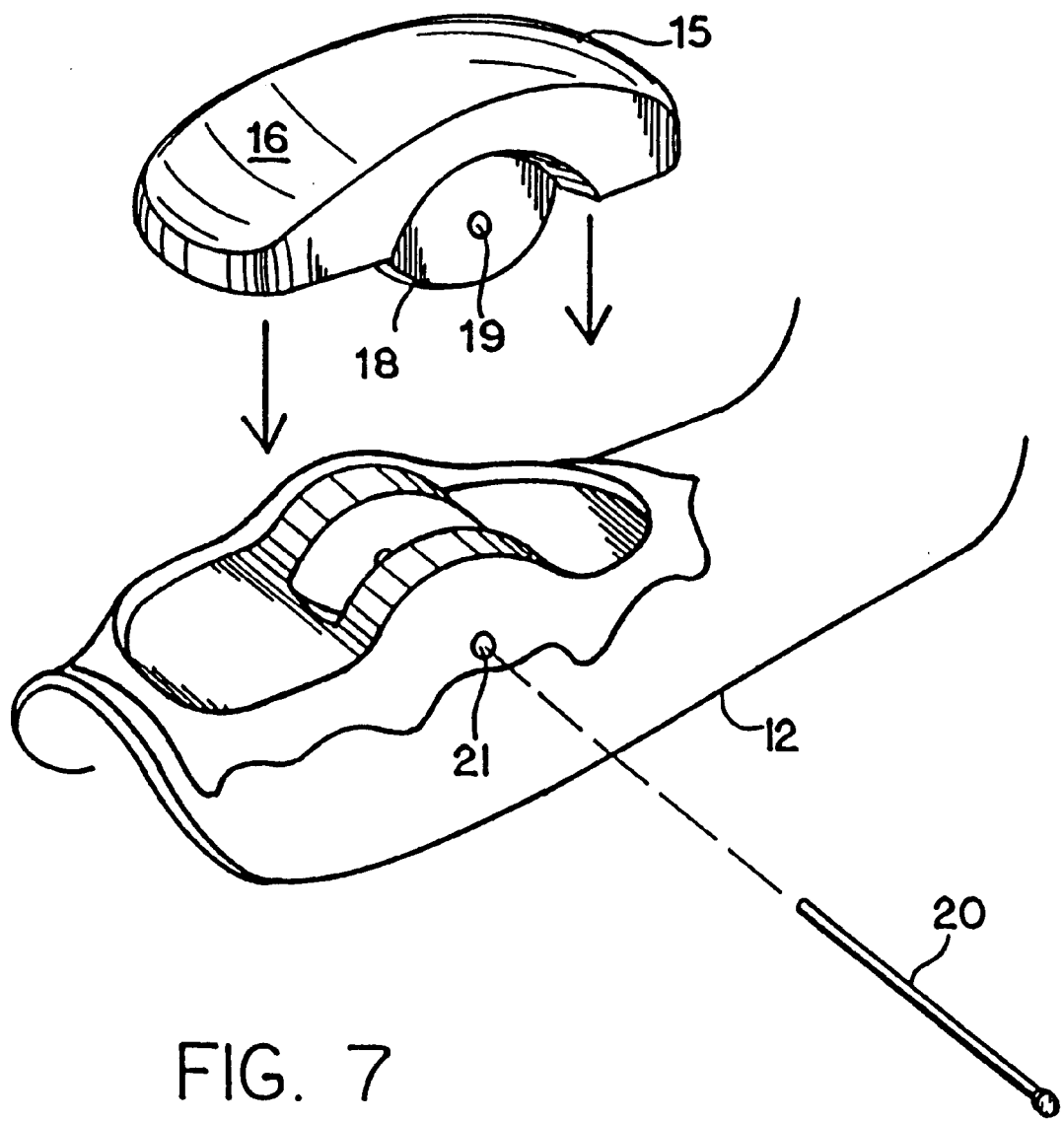
FIG. 7 is a side, perspective view depicting removal of an anchor wire in order to replace the bite plane with respect to the tray.

(7) As best shown in FIG. 7, each of the bite planes of the first embodiment is removable from the tray, and, for this purpose, an 0.036 inch stainless steel wire 20 is inserted through the aligned holes 19 in the tab 18 on the bottom of the bite plane and 20 and 21 in the lower tray, one on the right and one on the left side of the recess in the upper tray. (See FIG. 5C). A body of clear cold-cure acrylic A is applied to the bottom side 17 of each bite plane filling around the 0.036 inch stainless wire, but not the ends of the wire, which extend beyond the bonding acrylic and the lateral sides of the bite planes, and to the right and left posterior occlusal surfaces of the mandibular (lower) plastic base or tray.

(8) The fixture is then adjusted to lower the maxillary (upper) model/plastic tray down, over the mandibular (lower) model/plastic base to the preset position or 10 mm of vertical opening shown in FIG. 9, thereby trapping the body A of acrylic against the occlusal surface of the lower tray TL so that the tab 18 forms a complementary recess B in the body of acrylic (See FIG. 7). Additional cold-cure acrylic is applied to fill in and build up the gap between the bottom sides of the bite planes and posterior occlusal surfaces of the mandibular (lower) plastic tray right and left.

(9) The fixator is then immersed in warm water within an acrylic A pressure pot and cured at 2.5 bar for 10 minutes or longer. The cold-cure acrylic will conform, but not bond, to the bottom side of each bite plane. It will conform tightly around, but not bond to, the stainless steel wire 20 inserted through the retention holes of each bite plane, and will bond to, or become part of, the mandibular (lower) plastic tray. Therefore, by removing the stainless wire, the bite plane may be lifted from the recess, and replaced by other bite planes with like bottom sides, but with different heights to vary the vertical spacing between the trays. Although the bite planes used in fabrication cannot be made of a plastic which will bond with cold-cure acrylic, the bite planes supplied to the doctor, and used by the patient, can be made of a plastic which will bond with cold-cure acrylic as it will not come in contact with uncured cold-cure acrylic. The bite planes supplied to the doctor are made of an injection molded plastic which offers outstanding intra-oral characteristics, i.e., non-deforming, low coefficient of friction, etc.

(10) To the outside and just below the posterior region of the sides of each removable bite plane of each lower tray, elastic retention hooks 14 and 14' are bonded with the same clear orthodontic acrylic. The lower (mandibular) model with the lower plastic tray 12 still thereon one, then cured in an orthodontic pressure pot.

(11) On the outside of the maxillary or upper tray 11, just distal (behind) to the cuspids, or canine teeth, elastic retention hooks 13 and 13' are bonded with clear orthodontic acrylic on each side, right and left. These retention hooks 13, 13' are to be placed as low as possible (near the occlusion) and equal distance right and left or longitudinally of to the lower (mandibular) elastic retention hooks 14, 14'. The upper (maxillary) model and tray 11 with bonded retention hooks is then cured in the pressure pot.

(12) The trays are then trimmed from the models along the score lines shown in FIGS. 8 and 9, polished and returned to the professional.

As stated earlier, the bite planes are removable. The 0.036 stainless steel wire 20 locks the bite plane in place. The bite planes are constructed in various thicknesses, for example, 8 mm, 10 mm, 12 mm, and 14 mm. By removing the stainless steel anchor wire pin, the original bite plane may be removed, and a thinner, or thicker, bite plane inserted.

Second Office Visit

The professional tries standard bite planes intended to create the 10 mm vertical opening. Information is obtained from the patient as to any pressures on the teeth or gingiva. Also, the appliance is checked for comfort of and evenness of opening from side to side with the patient. If pressures are felt by the patient on any tooth or any area of the gingiva, then these areas must be carefully relieved. The only reasons there would be pressure on the teeth or gums are the following: (1) inaccurate impression; (2) warped model; or (3) tooth movement or dental work since the impression was taken.

When there is no pressure on teeth or gingiva, an elastic band B is stretched to attach its opposite ends over the buttons of the elastic retention hooks on each side. Due to its length and/or elasticity, the bands will advance the jaw the desired amount. The proper size elastic to advance the mandible 8 mm in the beginning may be used, unless the patient complains of discomfort.

Figure 10:
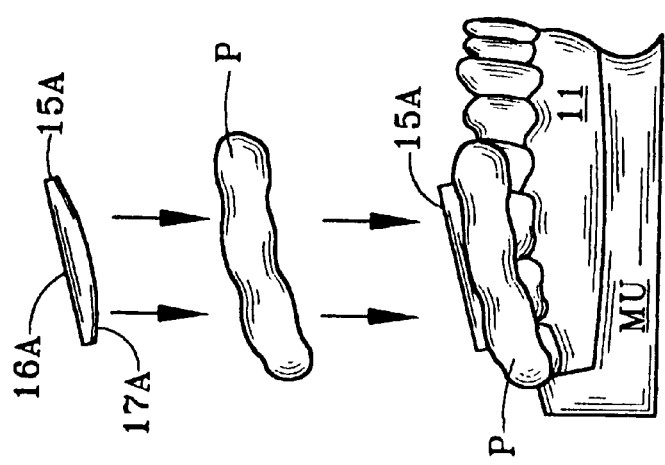
FIG. 10 is a side view of the upper model and tray showing a bite plane made in accordance with the second embodiment of the invention, being temporarily attached to each side of the occlusal surfaces of the upper tray.

As previously described, the second embodiment of the oral appliance of the present invention is of different construction than the first embodiment in that the bite planes thereof are fixed to the posterior occlusal surfaces of the lower tray. Thus, as shown in FIG. 10, the bite plane 15A has a flat bottom side 17A adapted to be secured to the posterior occlusal surface of each side of the lower tray, and a smoothly curved top side 16A which is temporarily secured to the upper tray 11, as will be described to follow.

Also, and because of this different construction, the bite planes are of a material which bonds or adheres to the body of the cold-cure acrylic to secure it to the lower tray. Although not removable, as in the first embodiment, the bite or occlusal surfaces of the top sides of the bite planes may be trimmed in order to lower or reduce the vertical opening between the trays in use of the appliance. Thus, as also previously mentioned, as when first secured to the lower tray, the bite planes would normally be selected of a height somewhat greater than that expected to be ideal. In any event, however, upon formation of the appliance, it would appear generally similar to the appliance 10 shown in FIGS. 1 and 2, prior to installation of the elastic bands.

The lab procedure for forming the second embodiment of the oral appliance is initially similar to that described in connection with the first embodiment. Thus, after thermopressure forming clear plastic sheets (0.060 to 0.080 inch thickness) over mandibular and maxillary plaster models, the basic shapes of the upper and lower trays 11 and 12 are cut by a disc (approximately 1" in diameter) and tracing around the perimeter of the upper and lower trays. As shown, these score lines are made at the junction of the gum line and the teeth in all areas, excepting the palate area and here the cut runs across the posterior portion of the palate from molar to molar. The disc will actually cut through the plastic and slightly into the plaster model, resulting in a groove in the plaster model. The excess plastic that is not a part of the tray is removed, leaving the plaster model with the plastic tray on it. A later step will involve removing the plastic tray from the model and further polishing the perimeter of the tray.

Although their top sides 16A are smoothly curved, the bottom sides 17A of bite planes 15A of the second embodiment are essentially flat, and in case, do not have a tab depending therefrom. Thus, as will be described to follow, the bite planes are not removable, but instead are fixedly secured to the occlusal surface of the lower tray, generally in the same location as the removable bit planes.

In the manner described with respect to the bite planes of the first embodiment, the left and right bite planes are positioned on the upper tray (while still on the model) with putty P (see FIG. 10), in contact with the posterior occlusal surfaces of the upper plastic tray covering the cusps of the molars and, or, bicuspids (posterior teeth). This step is done to accurately locate the bite planes in the contact with the right and left maxillary (upper) occlusal surfaces of the plastic upper tray. The putty P will harden to a rubber-like state and temporarily hold the bite planes in contact with the posterior occlusal surfaces of the upper tray in proper position.

Figure 12:
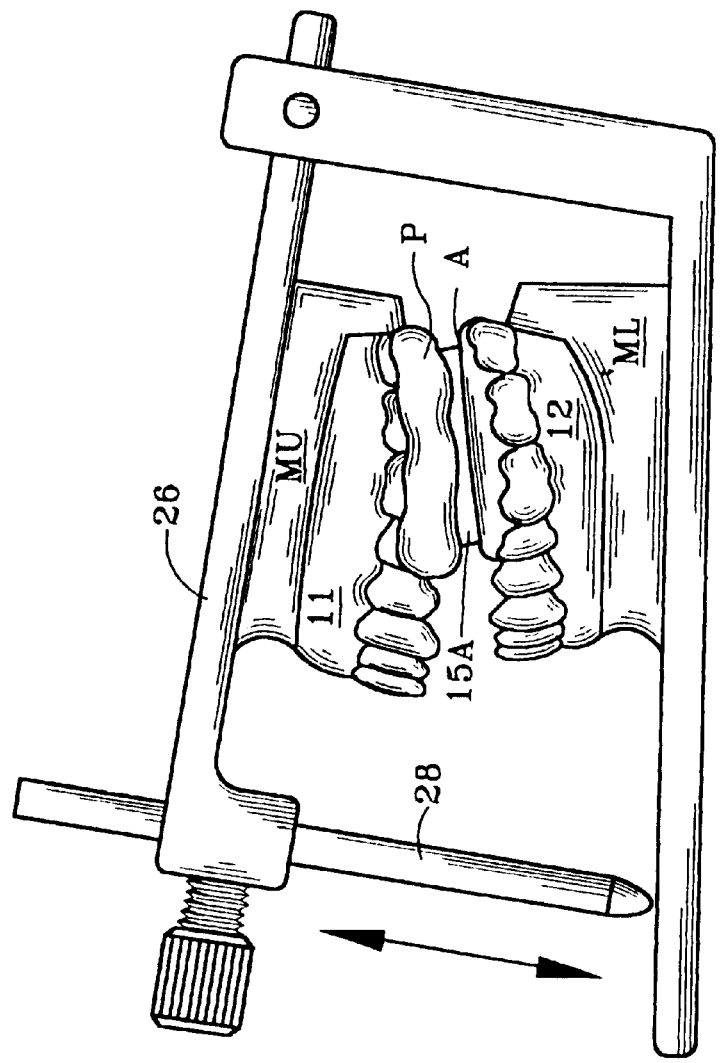
FIG. 12 is a view of the fixture with models and trays mounted thereon and the arm swung downwardly to engage the body of acrylic with the occlusal surfaces on each side of the lower tray.

The adjustable rod 28 on the fixator is made longer so as to open the bite (move the anterior teeth apart 10 mm) when the fixator is closed (See FIG. 12). This creates a space in the posterior region large enough to place the bite planes 15' between the maxillary and mandibular trays, and enough space for the cold-cure acrylic A to bond the bite planes to the mandibular lower tray.

The maxillary and mandibular models with the cut out plastic trays in position, and the bite planes held onto the posterior occlusal right and left surfaces of the upper tray with putty, are returned to the fixture. With its vertical opening set at 10 mm, the fixture is fully opened, as shown in FIG. 11, to allow access to the bottoms of the bite planes.

As shown in the same figure, orthodontic cold-cure acrylic A is applied to the exposed bottom sides of the bite planes. The acrylic is built up by alternately adding powder and liquid. Care is taken to keep the acrylic on the bottoms of the bite planes. The putty will help prevent the acrylic from running onto the upper plastic tray.

Figure 11:
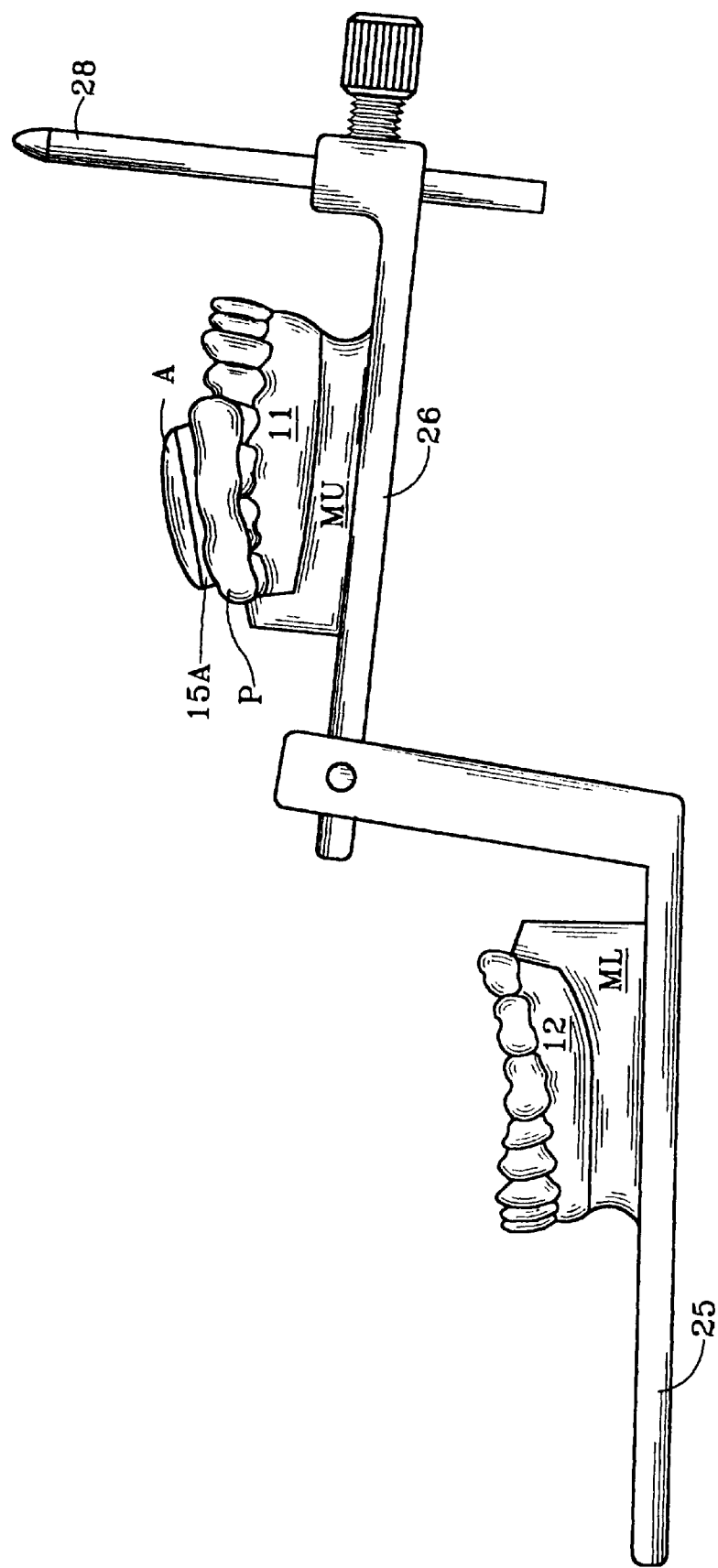
FIG. 11 is a side view of the upper tray of FIG. 10 with a body of acrylic on the bottom surfaces of the bite planes and mounted on an arm of a fixture for swinging toward a lower tray mounted on the base of the fixture.

As shown in FIG. 11, the fixture is then closed to the set vertical position, and the uncured acrylic will flow to fill the gap between the bite planes and posterior right and left surfaces of the lower plastic tray. The uncured acrylic is now in contact with the bottom sides of the bite planes (which are in proper position with upper tray) and the posterior occlusal right and left surfaces of the lower plastic tray.

The fixture with the models trays and bite planes are placed into an acrylic pressure curing pot for a length of time sufficient for the acrylic to "cure", or harden. Once the acrylic is hard, the bite planes are permanately joined on the lower tray, and will contact the posterior occlusal right and left surfaces of the upper tray, holding the vertical opening at 10 mm.

Although not shown, it will be understood that the retention hooks are secured to the outer sides of the upper tray and to the outer sides of bite planes 15A in much the same manner described in connection with the first embodiment.

The fixture may then be opened up to permit the trays to be removed from the models and then separated therefrom and polished. The putty permits the occlusal surfaces of the upper tray to release from the bite plane.

By its design, the elastic mandibular advancement appliance of both embodiments of this invention maintains infinite adjustability (by doctor or patient). Thus, by increasing the force of the elastics, the lower jaw is gently pulled forward to a position which increases the opening of the airway at the base of the tongue for increased air flows, just enough to significantly reduce or stop snoring, which is vibrations of soft tissues within the pharyngeal airway, and sleep apnea, which is the tongue falling back against the pharynx and stopping air flow.

The elastic mandibular advancement appliance never advances the mandible to a "fixed" position, due to the forgiving nature of elastics. Balance between right and left side muscles and right and left side temporomandibular joints remains flexible at all times, allowing the patient to seek the most comfortable, natural position while the elastic mandibular advancement appliance is worn. In contrast to other appliances in this area, the elastic mandibular advancement appliance is of minimal bulk. In summary, the elastic mandibular advancement appliance of the present invention is set apart by the use of elastics—yielding a completely adjustable, forgiving appliance, which is in many ways far more comfortable then anything else available. Therapeutically, by being able to adjust the bite opening, the doctor or patient may fine tune the elastic mandibular advancement appliance at any time to achieve the desired results.

What is claimed is:

1. A method of making a dental appliance which is adapted to advance a patient's lower jaw, comprising the steps of:

placing sheets of plastic over models of the patient's upper and lower teeth in a thermo-pressure machine so as to form upper and lower plastic trays adapted to fit over the teeth of the patient, trimming excess plastic material from the trays, mounting the models with the trays on a fixture with the occlusal surfaces of the trimmed trays in centric occlusion and spaced relation, and temporarily attaching the top side of each of a pair of bite plates to the occlusal surfaces of one of the trays, placing a body of acrylic upon the bottom sides of the bite planes and the occlusal surfaces of the other tray, closing the fixture so as to move the models and trays toward one another to a predetermined spaced position so that the acrylic flows over the occlusal surface of the other tray, placing the fixture in a pressure pot to cure the acrylic and thus secure the bottom sides of the bite planes to the occlusal surfaces of the other tray, removing the fixture from the pressure pot when the acrylic is cured, opening the fixture to move the models apart in order to release the top sides of the bite planes from their temporary attachment to the occlusal surface of one tray, and securing attachment parts to both trays with those on the upper trays being forward of those on the lower tray, whereby, upon removal of the trays from the models, and attachment of the ends of each of a pair of bands of selected length and/or elasticity to the attachment parts on both trays, the lower jaw of the patient is caused to move forwardly with the lower tray when the trays are installed on the patient's teeth.

2. As in claim 1, wherein the attachments parts are secured to the outer sides of the bite planes.

3. As in 2, wherein the other tray is the lower tray.

4. As in 1, wherein the acrylic bonds the bite planes to the other tray.

5. As in 1, wherein each bite plane is releasably attached to the body of hardened acrylic.

6. As in 5, wherein each bite plane is of such material that it does not bond to the acrylic, whereby upon release of the attachment, it may be removed from the other tray for replacement or repair.

7. As in 1, wherein the releasable attachment is a tab on the bottom side of the bite plate which, when th e trays are moved toward one another, forms a recess in the acrylic, and which has a hole through which a wire extends, the acrylic not bonding to the wire so that the wire may be removed from the holes in the tabs and formed in the acrylic, whereby, upon release of the attachment, the bite planes may be removed for replacement or repair.

8. An oral appliance for use in advancing a patient's lower jaw, comprising upper and lower trays adapted to fit tightly but removably over the occlusal surfaces of the upper and lower teeth of the patient, a bite plane on the occlusal surfaces of the trays having a bite surface which protrudes from the occlusal surfaces of the side of the one tray so as to engage the occlusal surfaces on the other tray and thus maintain the occlusal surfaces of the trays in predetermined spaced relation, when the trays are so fitted, a pair of elastic bands, and means by which the ends of each band may be releasably attached to the forward and the rearward portions of the opposite sides of the upper and lower trays, respectively, each band being of such length and/or elasticity that, when its ends are so attached to the fitted trays, and the trays are fitted over the patient's upper and lower teeth, the lower tray and jaw are advanced forwardly with respect to the upper tray and jaw.

9. As in 8, wherein the bite planes are on the lower tray.

10. As in 8, wherein the bite planes are removably mounted on the one tray.

11. As in 10, wherein each side of the one tray has a recess therein, each bite plane has a part for fitting closely in the recess in order to releasably secure the bite plane.

12. As in 10, wherein there are a plurality of pairs of removable bite planes each having its bite surface at a different elevation with respect to the occlusal surfaces of the tray on which it's mounted.

13. As in 8, wherein the bite planes are fixedly mounted on the occlusal surfaces of the lower tray.

14. As in 8, wherein the means by which the ends of the bands may be releasably attached comprises hooks on the outer sides of each tray.

15. As in 14, wherein the bands have holes in their ends for disposal over the hooks.

16. As in 8, wherein the means by which the ends of the bands may be releasably attached are fixedly mounted on the outer sides of the bite planes.

17. As in 8, wherein there are a plurality of pairs of elastic bands, with the bands of each pair being of different length and/or elasticity than those of each other pair.

18. A method of fitting a patient for an oral appliance adapted to advance the patient's lower jaw, comprising the steps of:

obtaining a pair of upper and lower trays adapted to fit, respectively, over the occlusal surfaces of the upper and lower teeth of a patient, wherein one tray has bite planes each secured to the occlusal surfaces thereof, and there are attachment parts on both sides of each tray with the attachment parts on the upper tray being forward of the attachment parts on the lower tray when the trays are so fitted, and attaching the ends of each of a pair of elastic bands to the upper and lower attachment parts on each side of the tray, wherein the bands are of such length and/or elasticity that, upon fitting of the upper tray on the patient's upper teeth, and movement of the lower tray and jaw forwardly to fit over the patient's lower teeth, the lower teeth and jaw are pulled forward a desired distance beyond their normally occluded position.

19. A kit for use in preparing and fitting a patient for an oral appliance which is adapted to advance a patient's lower jaw, comprising:

a pair of plastic sheets each adapted to be formed into a tray for fitting each of upper and lower models of a patient's teeth, a pair of bite planes each having a bottom side adapted to be secured to the occlusal surfaces of one tray and a top side for sliding over the occlusal surfaces of the other tray, and a pair of attachment parts each adapted to be secured to the outer side of one of the upper and lower trays, so that, upon attachment of the ends of elastic bands of the same length and elasticity attached to the attachment parts on each side of the upper and lower trays, whereby, and upon placing of the trays on the patient's teeth, the elastic bands are stretched so that the lower jaw of the patient is pulled forwardly a desired extent.

20. As in claim 19, wherein each attachment part is a hook having an enlarged head, over which a hole in the end of a band is adapted to snap.

21. For use in installing an oral appliance which includes upper and lower trays adapted to fit the upper and lower teeth, respectively, of a patient, and a bite plane on the occlusal surfaces of both sides of one tray, a kit comprising two pairs of hooks with each pair being adapted to be secured to outer sides of one of the trays with those on the upper tray being forward of those on the lower tray when the trays are so fitted, and a pair of elastic bands each having a hole in its opposite ends adapted to be snapped over the forward hook of the upper tray and the rearward hook of the lower tray, and a mid section intermediate its opposite ends which is thinner than its ends.

22. As in 21, wherein there are a plurality of pairs of bands each pair being of different length and/or elasticity.

23. An oral appliance, comprising upper and lower trays adapted to fit tightly but removably over the occlusal surfaces of the upper and lower teeth of a patient, a bite plane on the occlusal surface of both sides of the one tray each having a bite surface which protrudes therefrom so as to engage the occlusal surfaces on the other tray and thus maintain the occlusal surfaces of the trays in predetermined spaced relation, when the trays are so fitted, a pair of flexible bands, and means by which the ends of each band may be releasably attached to the anterior and the posterior portions of each opposite side of the upper and lower trays, respectively, each band being of such length and/or elasticity, that, when its ends are so attached, and the trays are fitted over the patient's teeth, the lower tray and thus the patient's lower jaw are advanced forwardly with respect to the upper tray and jaw.

24. As in claim 23, wherein the bite planes are removably mounted on the one tray.

25. As in claim 23, wherein the one tray is the lower tray.

26. As in claim 24, wherein
the bite planes are removably mounted on the lower tray.

27. As in claim 25, wherein
there are a plurality of pairs of removable bite planes with each pair having its bite surface at a different elevation with respect to the occlusal surfaces of the other tray.

28. As in claim 23, wherein
there are a plurality of removable bite planes with each pair having its bite surface at a different elevation with respect to the occlusal surfaces of the lower tray.

29. As in claim 23, wherein
there are a plurality of pairs of bands with each pair of such length and/or elasticity that the lower jaw is advanced a different distance.

30. As in claim 23, wherein
each band is elastic.

31. An oral appliance, comprising
upper and lower trays adapted to fit tightly but removably over the occlusal surfaces of the upper and lower teeth of a patient, a bite plane on the occlusal surfaces of both sides of one tray each having a bite surface which protrudes therefrom so as to engage the occlusal surfaces on the other tray and thus maintain the occlusal surfaces of the trays in predetermined spaced relation, when the trays are so fitted, and band means releasably attached to the anterior and posterior portions of both sides of each tray and being of such length and/or elasticity that the lower tray and thus the lower jaw are advances forwardly when the trays are fitted over the patient's teeth.

32. As in claim 31, wherein
the band means is releasably attached to the bite plane.

33. As in claim 31, wherein
the bite planes are removably mounted on one of the trays.

34. As in claim 31, wherein
the bite planes are on the posterior portions of the lower tray.

35. A method of fitting a patient for an oral appliance adapted to advance the patient's lower jaw, comprising the steps of:

obtaining a pair of upper and lower plastic trays adapted to fit, respectively, over the occlusal surfaces of the upper and lower teeth of a patient, with one tray having bite planes on the posterior portions of the occlusal surfaces on their right and left sides, and attaching the ends of a band to the anterior portions of each side of the upper tray and to the bite planes, wherein the bands are of so constructed that, upon fitting of the upper tray on the patient's upper teeth, and the lower tray on the patient's lower teeth, the patient's lower teeth are moved forwardly a desired distance beyond their normally occluded positions with respect to the upper teeth.

36. A kit for use in preparing an oral appliance is adapted to advance a patient's lower jaw, comprising:

a pair of plastic sheets each adapted to be formed by heat and pressure into a tray for fitting each of upper and lower models of a patient's teeth, a pair of bite planes each having a bottom side adapted to be secured to the posterior occlusal surfaces of one tray tray and a top side for sliding over the occlusal surfaces of the other tray, and a pair of attachment means each adapted to be secured to the anterior portion of one side of the other tray, so that, upon attachment of the ends of each of a pair of flexible bands to the first and second attachments means on each side of the upper and lower trays, and fitting the trays on the patient's upper and lower teeth, the lower tray and thus the lower jaw of the patient are pulled forwardly a desired extent with respect to the upper tray and jaw.

37. As in claim 36, wherein
the bite planes have means by which they may be removably mounted on the one tray.

38. As in claim 36, wherein
there are a plurality of pairs of bite planes of different heights.

39. A method of making an oral appliance which is adapted to advance a patient's lower jaw, comprising the steps of:

placing sheets of plastic over models of the patient's upper and lower teeth in a thermo-pressure machine so as to form upper and lower plastic trays adapted to fit over the teeth of the patient, trimming excess plastic material from the trays, mounting the models with the trays on a fixture with the occlusal surfaces of the trimmed trays in centric occlusion and spaced relation, and temporarily attaching the top side of each of a pair of bite plates to the occlusal surfaces of the upper tray, placing a body of acrylic between the bottom sides of the bite planes and the occlusal surfaces of the lower tray, closing the fixture so as to move the models and trays toward one another to a predetermined spaced position so that the acrylic flows over the occlusal surfaces of the lower tray, to secure the bite planes to that tray, placing the fixture in a pressure pot to cure the acrylic and thus bond the bottom sides of the bite planes to the occlusal surface of the lower tray, removing the fixture from the pressure pot when the acrylic is cured, opening the fixture to move the models apart in order to release the top sides of the bite planes from their temporary attachment to the occlusal surface of the upper tray, and securing attachment parts to the sides of both trays with those on the upper tray being forward of those on the lower tray, whereby, upon removal of the trays from the models, and attachment of the ends of each of a pair of flexible bands of selected construction to the parts on the sides of both trays, the lower jaw of the patient is caused to move forwardly when the trays are fitted to the patient's teeth.

* * * * *